(12) United States Patent
Tietze et al.

(10) Patent No.: US 9,012,543 B2
(45) Date of Patent: Apr. 21, 2015

(54) BENZOXAZINE COMPOUNDS DERIVATED FROM PHENOLPHTHALEIN HAVING FLAME-RETARDANT PROPERTIES AND A PROCESS FOR THEIR PREPARATION

(75) Inventors: Roger Tietze, The Woodlands, TX (US); Dave Orser, Lodi, NJ (US); Yefim Blyakhman, Brooklyn, NY (US); Mark Bryant, The Woodlands, TX (US); Bor-Sheng Lin, Berkeley Heights, NJ (US)

(73) Assignee: Huntsman Advanced Materials Americas LLC, The Woodlands, TX (US)

( * ) Notice: Subject to any disclaimer, the term of this patent is extended or adjusted under 35 U.S.C. 154(b) by 2166 days.

(21) Appl. No.: 11/663,879

(22) PCT Filed: Sep. 27, 2005

(86) PCT No.: PCT/EP2005/054827
§ 371 (c)(1),
(2), (4) Date: Mar. 8, 2011

(87) PCT Pub. No.: WO2006/035021
PCT Pub. Date: Apr. 6, 2006

(65) Prior Publication Data
US 2011/0152453 A1 Jun. 23, 2011

Related U.S. Application Data

(60) Provisional application No. 60/613,829, filed on Sep. 28, 2004.

(51) Int. Cl.
C08H 7/00 (2011.01)
C09K 21/00 (2006.01)
C08K 5/357 (2006.01)
C07D 413/14 (2006.01)
C09K 21/10 (2006.01)
H05K 1/03 (2006.01)

(52) U.S. Cl.
CPC .............. C08K 5/357 (2013.01); C07D 413/14 (2013.01); C09K 21/10 (2013.01); *H05K 1/0373* (2013.01)

(58) Field of Classification Search
CPC ........ C08K 5/357; C09K 21/10; C07D 413/14
USPC .................. 524/74, 700; 252/182.11, 182.12, 252/182.13, 601, 609; 156/242
See application file for complete search history.

(56) References Cited

U.S. PATENT DOCUMENTS

| 3,944,583 | A | 3/1976 | Quinn |
| 5,152,939 | A | 10/1992 | Ishida |
| 5,152,993 | A | 10/1992 | Bjursten et al. |
| 5,200,452 | A * | 4/1993 | Schreiber ...................... 524/398 |
| 5,266,695 | A | 11/1993 | Ishida |
| 5,543,516 | A | 8/1996 | Ishida |
| 6,482,946 | B1 * | 11/2002 | Dettloff et al. .................. 544/73 |
| 6,558,783 | B1 * | 5/2003 | Kato et al. ................. 428/297.4 |
| 6,645,631 | B2 * | 11/2003 | Gan et al. ...................... 428/413 |
| 8,062,455 | B2 * | 11/2011 | Tsuei ............................. 156/242 |
| 2010/0330287 | A1 * | 12/2010 | Tietze et al. .................. 427/386 |

FOREIGN PATENT DOCUMENTS

| EP | 356379 A | 2/1990 |
| EP | 458739 A | 11/1991 |
| EP | 1366053 A | 12/2003 |
| JP | 2001220455 A | 8/2001 |
| WO | WO 99/18092 A | 4/1999 |
| WO | WO 00/61650 A | 10/2000 |
| WO | WO 01/34581 A | 5/2001 |

OTHER PUBLICATIONS

Yang et al. "Synthesis and curing behavior of a benzoxazine based on phenolphthalein and its high performance polymer", J Polym Res, 2011, 18, 1725-1733. published online Feb. 25, 2011.*
Li et al. "Preparation and properties of copolymer resins based on phenolphthalein benzoxazine-benzoic acid and bisoxazoline", J Therm Anal Calorim, 2013, 113, 633-639. published online Oct. 21, 2012.*
STIC structure search, Nov. 8, 2012.*

* cited by examiner

*Primary Examiner* — Jane L Stanley

(57) ABSTRACT

The instant invention relates to 3,3'-bis(3,4-dihydro-3-phenyl-2H-1,3-benzoxazin-6-yl)-1(3H)-isobenzofuranone and analogues based on phenolphthalein, formaldehyde and a primary amine. Such compounds are, when cured to form polymeric networks, difficultly inflammable and resistant to high temperatures. Such compounds may especially be used in the production of printed wiring boards.

8 Claims, No Drawings

BENZOXAZINE COMPOUNDS DERIVATED FROM PHENOLPHTHALEIN HAVING FLAME-RETARDANT PROPERTIES AND A PROCESS FOR THEIR PREPARATION

CROSS REFERENCE TO RELATED APPLICATIONS

This application is the National Phase of International Application PCT/EP2005/054827 filed Sep. 27, 2005 which designated the U.S. and which claims priority to U.S. Pat. App. Ser. No. 60/613,829 filed Sep. 28, 2004. The noted applications are incorporated herein by reference.

TECHNICAL FIELD

This invention relates to benzoxazine compounds and varnishes which may be cured to form polymeric networks which are difficultly inflammable and resistant to high temperatures, as well as to the use of such polymeric resins. More particularly, this invention relates to 3,3'-bis(3,4-dihydro-3-phenyl-2H-1,3-benzoxazin-6-yl)-1(3H)-isobenzofuranone and analogues based on phenolphthalein, formaldehyde and a primary amine.

BACKGROUND OF THE INVENTION

Benzoxazine compounds have been employed satisfactorily to produce prepregs, laminates, PWB's, moulding compounds, sealants, sinter powders, cast articles, structural composites parts and electrical and electronic components by impregnating operations and infusion processes. Such resins are dimensionally stable and have good electrical and mechanical resistance, low shrinkage, low water absorption, medium to high glass transition temperatures and good retaining properties, in terms of mechanical properties.

Benzoxazine compounds can be produced in several ways. First of all, by using a process based on solvents cf. U.S. Pat. No. 5,152,993 or U.S. Pat. No. 5,266,695. Secondly, as for example described in U.S. Pat. No. 5,543,516, the preparation of benzoxazines is disclosed without using solvents.

The flame resistance, despite the fact that it compares favorably with that of other polymeric resins resistant to high temperatures, such as for instance epoxy resins is still not sufficient for many uses. In order to make benzoxazines flame retardant the addition of bromine, phosphorous, chlorine containing compounds, fillers or the use of special flame retarded backbones in benzoxazines as it is described for example in EP 0458739, EP 356 379, U.S. Pat. No. 5,200,452, U.S. Pat. No. 5,152,939 or in EP 1366053, JP2001220455 is necessary. Very often the offered solutions to make a composition flame retardant is based on inert fillers or halogen containing compounds or other additives which have as a rule one or several drawbacks:

They are not soluble in solvents and hence cause problems in terms of processing.
They show poor oxidative stabilities at elevated temperatures.
Additives are very often responsible for a decrease of the glass transition levels.
Very often poor physical properties of the cured resins are been observed, cf. U.S. Pat. No. 512,939.
Toxic gases of combustion may form in case of fire, especially when halogenated compounds are present.

SUMMARY OF THE INVENTION

It now has surprisingly been found that articles made from specific benzoxazine compounds, formally derived from phenolphthalein, formaldehyde and a primary amine, show a greatly improved flammability while the mechanical properties are maintained. Such benzoxazine compounds are therefore particularly suitable for use in aerospace, industrial, electronics or other applications such as automotive, adhesives, sealants, prepregs and laminates, coatings and PCB's. They can also be processed by using infusion techniques such as RTM or VaRTM.

DETAILED DESCRIPTION OF THE INVENTION

A first aspect of the present invention is a compound of the general formula

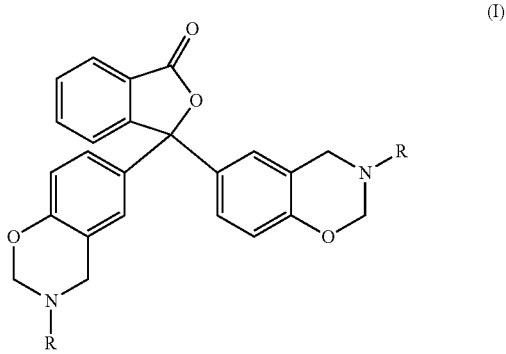

(I)

wherein R is, independently from one another, allyl, unsubstituted or substituted phenyl, unsubstituted or substituted $C_1$-$C_8$-alkyl or unsubstituted or substituted $C_3$-$C_8$-cycloalkyl. Suitable substituents on said R-groups include amino, $C_1$-$C_4$-alkyl and allyl. Typically, one to four substituents may be present on said R-group.

Preferably both substituents R are the same and especially preferred phenyl.

Another aspect of the present invention is a benzoxazine compound obtainable by reacting, under removal of water, phenolphthalein with formaldehyde and a primary amine, whereby the molar ratio of phenolphthalein and formaldehyde is from 1:3 to 1:10, preferred from 1:4 to 1:7, particularly preferred from 1:4.5 to 1:5 and the molar ratio of phenolphthalein and the primary amine groups is from 1:1 to 1:3, preferred from 1:1.4 to 1:2.5, particularly preferred from 1:2.1 to 1:2.2

The reaction time can vary widely with reactant concentration, reactivity and temperature. Times desirably vary from a few minutes for solventless to a few hours, e.g. 2 or 10 for diluted reactants. If a water based solution of formaldehyde is used as one reactant then a water miscible organic solvent is sometimes desirable. If one or more reactant is a liquid it may be used to dissolve the other components. If all of the components are solids they may be premixed as solids and then melted or first melted and then mixed. The temperature of reaction can be determined by routine experimentation noting the formation of benzoxazine and less desired products and optimizing temperature and time for a desirable product. Desirable temperatures are from about 0° C. to about 250° C., preferably from about 0 or 50° C. to about 150° C., and most preferred from about 80° C. to about 120° C.

The benzoxazine synthesis reaction may be conducted at atmospheric pressure or at a pressure up to about 100 psi. In some instances, a reaction carried out under pressure constitutes a preferred mode since fewer byproducts are produced. When a polyfunctional benzoxazine is being prepared, higher pressures generally results in relatively higher amounts of difunctional benzoxazine monomers.

The ultimate reaction mixture contains the desired benzoxazine monomer, which may be present as an open ring structure depending, for example, on the ratio of educts, and oligomers thereof, as well as impurities. If desired, the mixture may be purified to obtain a more concentrated form of the product described, for example by well-known crystallization or solvent washing techniques.

Examples of primary amines that are particularly useful include:

Aromatic mono- or di-amines, aliphatic amines, cycloaliphatic amines and heterocyclic monoamines; specifically, Aniline, o-, m- and p-phenylene diamine, benzidine, 4,4'-diaminodiphenyl methane, cyclohexylamine, butylamine, methylamine, hexylamine, allylamine, furfurylamine ethylenediamine, and propylenediamine. The amines may, in their respective carbon part, be substituted by $C_1$-$C_8$-alkyl or allyl.

Preferred primary amines are according to the general formula $RNH_2$ (II), wherein R is allyl, unsubstituted or substituted phenyl, unsubstituted or substituted $C_1$-$C_8$-alkyl or unsubstituted or substituted $C_3$-$C_8$-cycloalkyl. Suitable substituents on said R-group include amino, $C_1$-$C_4$-alkyl and allyl. Typically, one to four substituents may be present on said R-group.

Preferably R is phenyl.

Preferably, the reaction is carried out in the absence of a catalyst.

Typically the reaction is carried out in a solvent. Suitable solvents include: aromatic solvents, like toluene and xylene, dioxane, ketones, like methylethylketone, methyl-isobutylketone, and alcohols, like isopropanol, sec-butanol and amyl alcohol. The solvents may also be used as a solvent mixture. Particularly suitable solvents are toluene and sec-butanol. However, in analogy to known reactions from the literature, a solvent may be dispensed with.

By thermally curing said benzoxazine compounds at temperatures above 100° C., preferably at a temperature from 140° to 220° C., difficultly inflammable (flame retarded) polymeric resins are obtained.

Another aspect of the present invention is the use of a benzoxazine compound, as described before, in the process of preparation of flame retarded castings, prepregs or laminates and infusion systems as well.

Flame retarded in the context of the present invention means, preferably, meeting the UL 94 standard ("Underwriters Laboratory" test method UL 94) criterion V0.

The properties of the polymeric resins produced as described above can be tailored for certain applications by addition of usual additives. The following additives are of particular importance:
reinforcement fibers, such as glass, quartz, carbon, mineral and synthetic fibers (Keflar, Nomex), natural fibres, such as (flax, jute, sisal, hemp) in the usual forms of short fibers, staple fibers, threads, fabrics or mats;
plasticizers, especially phosphorus compounds;
carbon black or graphite;
fillers;
dyestuffs;
micro hollow spheres;
metal powders.

The processes known for thermosetting resins, such as phenol formaldehyde resins or epoxy resins, such as hot-pressing of prepregs, SMC (Sheet Molding Compound); or molding; casting; filament winding; infusion techniques or vacuum impregnating (RTM, VaRTM) are suitable for processing the resins according to the invention. With respect to vacuum impregnating, very fine additives having a particle size of 0.2 to 0.001 mm are particularly suitable.

Another aspect of the present invention is a laminating composition comprising 30 to 80% by weight, preferably 60 to 70% by weight, of a benzoxazine compound as described above. In addition, the laminating composition will typically contain a solvent or solvent mixture, a catalyst or a combination of catalysts and a flame retardant.

The weight of a flame retardant used in a formulation will depend upon the effectiveness of that component in the formulation in achieving the desired V0 criterion according to UL-94 standard. A weight range of 0.1 to 50 parts by weight has to be taken into account.

Examples of solvents that are particularly suitable include methylethylketone, acetone, N-methyl-2-pyrrolidone, N,N-dimethyl formamide, pentanol, butanol, dioxolane, isopropanol, methoxy propanol, methoxy propanol acetate, dimethylformamide, glycols, glycol acetates and toluene, xylene. The ketones and the glycols are especially preferred. Typically, the laminating composition will contain 20 to 30% by weight, preferably 30% by weight, of a solvent.

Examples of catalysts that are particularly suitable include thiodipropionic acid, phenols, thiodiphenol benzoxazine and sulfonyl benzoxazine, sulfonyl diphenol. Certain flame retardants, for example Fyroflex PMP and CN 2465, will act as catalysts. The catalyst concentration will also depend on the effectiveness of that component in achieving the desired reactivity. Typically, the laminating composition will contain 0.001-2, preferably 0.1-2% by weight of a catalyst Examples of flame retardants that are particularly suitable include: phosphorous flame retardants, such as DOPO (9,10-dihydro-9-oxa-phosphaphenanthrene-10-oxide), fyroflex PMP (Akzo; a reactive organophosphorus additive modified with hydroxylgroups at its chain ends and able to react with epoxy resins), CN2645A (Great Lakes; a material which is based on phosphine oxide chemistry and contains phenolic functionality able to react with epoxy resins), and OP 930 (Clariant), brominated polyphenylene oxide and ferrocene. Typically, the laminating composition will contain 0.1 to 50% by weight of a flame retardant. For example, for ferrocene an amount of about 2% by weight is particularly suitable.

Also, the laminating composition may contain an epoxy resin. The selection of the epoxy resins depends on the property enhancement that is needed. Typical epoxy resins that are especially useful are bisphenol A and bisphenol F based epoxy resins, epoxy cresol novolac, epoxy phenol novolac, Tactix 742, Tactix 556, and Taxtix 756, cycloaliphatic epoxy resins, PT 810, MY 720, MY 0500, etc. They may be used in amounts of about 2% to 60% by weight in the laminating composition.

Typically, the laminating compositions will contain about a minimum of 2 parts of epoxy resin to every 8 parts of benzoxazine up to a maximum of 9 parts of epoxy resin to one part of benzoxazine Beyond this, it is possible to incorporate fillers like ammonium polyphosphates and inorganic and organic phosphorus compounds a described in EP 356379 and U.S. Pat. No. 5,200,452.

The laminating compositions are useful to make electrical laminates and other composites from fibrous reinforcement and a matrix resin. Examples of suitable processes usually contain the following steps:
Solvent Based Impregnation Process (1) A benzoxazin-containing formulation is applied to or impregnated into a substrate by rolling, dipping, spraying, other known techniques and/or combinations thereof. The substrate is typically a woven or nonwoven fiber mat containing, for instance, glass fibers or paper.

(2) The impregnated substrate is "B-staged" by heating at a temperature sufficient to draw off solvent in the benzoxazin formulation and optionally to partially cure the benzoxazin formulation, so that the impregnated substrate can be handled easily. The "B-staging" step is usually carried out at a temperature of from 90° C. to 210° C. and for a time of from 1 minute to 15 minutes. The impregnated substrate that results from "B-staging" is called a "prepreg". The temperature is most commonly 100° C. for composites and 130° C. to 200° C. for electrical laminates.

(3) One or more sheets of prepreg are stacked or laid up in alternating layers with one or more sheets of a conductive material, such as copper foil, if an electrical laminate is desired.

(4) The laid-up sheets are pressed at high temperature and pressure for a time sufficient to cure the resin and form a laminate. The temperature of this lamination step is usually between 100° C. and 230° C., and is most often between 165° C. and 190° C. The lamination step may also be carried out in two or more stages, such as a first stage between 100° C. and 150° C. and a second stage at between 165° C. and 190° C. The pressure is usually between 50 N/cm$^2$ and 500 N/cm$^2$. The lamination step is usually carried out for a time of from 1 minute to 200 minutes, and most often for 45 minutes to 90 minutes. The lamination step may optionally be carried out at higher temperatures for shorter times (such as in continuous lamination processes) or for longer times at lower temperatures (such as in low energy press processes).

(5) Optionally, the resulting laminate, for example, a copper-clad laminate, may be post-treated by heating for a time at high temperature and ambient pressure. The temperature of post-treatment is usually between 120° C. and 250° C. The post-treatment time usually is between 30 minutes and 12 hours.

EXAMPLES

All tests were performed according to IPC TM 650.
The IPC test methods are the electrical laminate industry standard (The Institute For Interconnection and Pachaging Electronic Circuits, 3451 Church Street, Evanston, Ill. 60203) as follows:

| Method | IPC-Test Method Number: |
|---|---|
| Reactivity (varnish) | IPC-TM-650-5.410 |
| Rest Gel time at 170° C., seconds | IPC-TM-650-2.3.18 |
| Mil Flow, weight percent | IPC-TM-650-2.3.17 |
| Glass Transition Temp., $T_g$ [° C.] | IPC-TM-650-2.4.25 |
| Copper Peel Strength | IPC-TM-650-2.4.8 |
| Pressure Cooker Test, weight percent water pick-up & percent passed solder bath at 260° C. | IPC-TM-650-2.6.16 |
| UL-94 Standard | IPC-TM-650-2.3.10 |

A) Preparation of 3,3'-bis(3,4-dihydro-3-phenyl-2H-1,3-benzoxazin-6-yl)-1(3H)-isobenzofuranone In a 22 liters glass jacketed Belatec reactor fitted with an addition funnel, thermocouple and a condensor 3884.1 g (12.2 mol) of phenoplphthalein is charged. Subsequently the reactor is charged with 1721.5 g (59.3 mol) of paraformaldehyde, 2420 ml of xylene and 4840 ml of sec-butanol under stirring (ca. 350 rpm). That reaction mixture is preheated to 80° C.-82° C. with stirring.

2383.7 g (25.6 mol) aniline is added over a period of 45 min to 1 hour with simultaneous heating to the refluxing point at 94-95° C., maintaining intensive refluxing with separation of water.

When 25% of the solvents are removed, additionally 600 ml of xylene and 1200 ml sec-butanol are slowly added to the reaction mixture such that the drop of the reaction temperature is minimized. The xylene/sec.-butanol/water azeotrope distills at a higher temperature as the water is removed, so the temperature must be increased to maintain a steady distillation rate. After the water removal is complete, the condensor is replaced by with a distillation head and a receiver.

When the boiling temperature reaches a value of 100-105° C. (within 6-7 hours of the initial reflux), the water removal and condensation process is over, and the solvent distillation is started until the temperature of the solution is 120° C.-122° C. (no vacuum is applied). At this point the concentration of the solids is determined. At a concentration of 70.5% to 71.5% of solids the process is over and the product can be discharged or used for the preparation of the laminating composition in the same reactor.

Melting point: 98-103° C.
$^1$H-NMR (d$_6$ acetone):
$\delta$=4.59 ppm (s); $\delta$=5.4 ppm (s); $\delta$=6.5-7.3 ppm (m);
$\delta$=7.5 ppm (m);
Infrared spectrum (KBr pill) IR (neat): 3600 cm$^{-1}$-3150 cm$^{-1}$; 3100 cm$^{-1}$-3000 cm$^{-1}$; 2950 cm$^{-1}$; 2850 cm$^{-1}$; 1750 cm$^{-1}$; 1600 cm$^{-1}$; 1450 cm$^{-1}$; 1220 cm$^{-1}$; 1090 cm$^{-1}$; 950 cm$^{-1}$; 725 cm$^{-1}$; 650 cm$^{-1}$.

B) Neat Resin Castings

Neat resin castings for flammability testing are made from the benzoxazine obtained according to example A). The benzoxazine is melted, degassed and poured into a mold. The resin in the mold is then cured for 2 hours at 400° F. (215.5° C.) to produce a casting suitable for testing. These castings are evaluated for their flammability resistance and thermal properties.

Flammability testing is done by using a UL 94 flammability test chamber. The chamber is equipped with a Bunsen burner supplied with industrial grade methane.

All testing is done as per UL 94 test. Five specimens per sample are cut to 5 inch×0.5 inch×0.12 inch.

TABLE 1

| | UL 94 Flammability Testing of Neat Resin Castings | | | |
|---|---|---|---|---|
| Resin | 1$^{st}$ Burn Average Time, [s] | 2$^{nd}$ Burn Average time, [s] | Average Burn Length, [inch] | UL 94 rating |
| Bisphenol A benzoxazine | 31.0 | 19.2 | 4.2 | HB |
| Phenolphthalein benzoxazine | 4.9 | 2.0 | 0.3 | V0 |

The phenolphthalein benzoxazine casting (resin prepared according to Example A) meets the V0 criterion whereas a bisphenol A benzoxazine casting (resin prepared in analogy to Example A but replacing phenolphthalein with bisphenol A) failed.

C) Laminates

Benzoxazine fiberglass laminate composites are made by the solvent impregnating process. The benzoxazine is dissolved into a solvent along with a soluble catalyst and then coated onto 7628, an industry standard fiberglass weave type as defined by the glass strands, thickness and weight of the glass weave (Porcher SA, with a silane finish). The solvent is then evaporated and B-staged (Table 3). The prepreg with copper is then laminated under heat and pressure to produce a copper clad laminate. The temperature of the hot air in the oven is 150-180° C. and the times to generate the B-stage range in-between 2-5 seconds. The resin content ranges in-between 35-42%. These laminates are then evaluated for their thermal and flammability properties (Table 4).

All properties are based on 8 plies 7628 glass fabric laminate as per IPC TMI 3949, except for burning behavior and dielectric analysis. The laminates always have the fiberglass plies oriented such that all plies are laid in the same fill and warp direction.

TABLE 2

Laminating Compositons:

|  | A | B |
|---|---|---|
| 1-Pentanol | 3% |  |
| 1-Butanol |  | 3% |
| 2-Butanone | 27% | 27% |
| Ferrocene | 4% | 4% |
| 1,1,2,2-Tetrakis(4-glycidyloxy phenyl)ethane | 6% | 6% |
| 3,3-bis(3,4-dihydro-3-phenyl-2H-1,3-benzoxazin-6-yl)-1(3H)-isobenzofuranone | 60% | 60% |

To the composition, 2 parts by weight of methylimidazol is added as a catalyst.

Typical Solution Properties for A:

Viscosity: [cps]: 1000-3000

Solids [%]: 69-71

Appearance: clear amber liquid

Solvent: Methylethylketone and 1-Pentanol [up to 5%]

The composition A can be formulated with any solvent typically used to manufacture prepregs for PWB applications. Dilution can be done with acetone, MEK; glycols, glycol acetates, toluene, and other solvents.

Varnish compositon

| Component | Formulation |
|---|---|
| Composition A | 100 phr |
| 2-Methylimidazol | 0.4-0.8 phr |
| Varnish solids | 40-60% |
| Gel time 171° C., [s] | 150-200 |

TABLE 3

| Initial Press Temperature | room temperature |
|---|---|
| Heating rate, ° C./min | 3-5 |
| Pressure, psi | ≥100 |
| Final Press Temperature | 190° C.-200° C. |
| Time at press temperature | 120 minutes |
| Post cure [2 hours] | 240° C.-250° C. |

TABLE 4

| Test | Value |
|---|---|
| Thermal properties | |
| Glass Transition Temperature, ° C. | DSC 190-305 |
| | TMA 170-180 |

TABLE 4-continued

| | Test | Value |
|---|---|---|
| Thermal Oxidative Stability | | |
| T260 | TMA | >30 Minutes |
| T288 | TMA | >30 Minutes |
| Solder float at 260° C. degradation | >20 Minutes | pass/no |
| Decomposition | TGA | 325° C. |
| (Burning behaviour) | UL-94 | V0 |
| Chemical Properties: | | |
| Water absorption | 24 hours | 0.03% |
| Pressure cooker (2 atm, 121° C.) | 2 hours | pass |

Laminating Composition C

| Phenolpthalein Benzoxazine | 20% |
|---|---|
| Tactix 742 | 32% |
| GY281 | 12% |
| Fyroflex PMP | 12% |
| XB4399 | 4% |
| Methoxy propanol | 10% |
| MEK | 10% |
| Trithiotriazine | 0.5 phr |

Tactix742 is tris(phenylglycidylether)methane.

GY281 is bisphenol F epoxy resin.

Fyroflex PMP is a phosphorous based phenol Flame Retardant from Akzo.

XB4399 is 1,1,2,2-tetrakis(4-glycidyloxyphenyl)ethane.

Typical Solution Properties

| Viscosity, cps | 5000-10000 |
|---|---|
| Solids % | 79-81 |
| Appearance | Clear amber liquid |
| Solvent | MEK 10% & Methoxy propanol 10% |
| Epoxy Equivalent Weight | 450-550 [on solids] |
| Phosphorus content % | 2-3 |

Varnish Preparation

The system can be formulated with any solvent typically used to manufacture prepregs for PCB applications. To the varnish, 2-Methyl-imidazol is added as a catalyst. The recommended formulation is

| Component | Formulation |
|---|---|
| Formulation C | 100 phr |
| 2-Methylimidazol | 0.002-0.1 phr |
| Varnish solids | 50-65% |
| Gel time 171° C., [s] | 110-400 |

Dilution of the system can be performed with acetone, MEK, glycols, glycol acetates, and other solvents.

For optimum bonding between resin and glass, it is recommended that a glass fabric treated with a silane-sizing agent suitable for epoxy resins is used.

Typical Prepreg properties:

| Glass Cloth | 7628 |
|---|---|
| Finish | CS440 |
| Resin Content, % | 35-42 |
| Mil Flow, % | 15-20 |
| Gel Time at 171° C. | 75-110 |

Press Cycle:

| Initial Press Temperature | room temperature |
|---|---|
| Heating rate, °C./min | 3-5 min |
| Pressure, psi | 50-150 |
| Final Press Temperature | 205° C.-218° C. |
| Time at Press Temperature | 90-120 Minutes |

Laminate Properties:

All properties are based on 8 plies 7628 glass fabric laminate as per IPC TMI 3949, except for burning behavior and dielectric analysis for which neat resin castings are used as described above.

| | Test | Value |
|---|---|---|
| Thermal Properties | | |
| Glass Transition Temperature, °C. | DSC | 210-235 |
| Thermal Oxidative Stability | | |
| T260 | TMS | >60 minutes |
| T288 | TMA | >5 minutes |
| Solder float at 260° C. | >20 Minutes | pass |
| Solder Foat at 288° C. | 5 Minutes | pass |
| Decomposition, °C. | TGA | 340° C. |
| Burning Test | UL-94 | V0 |
| Chemical Properties | | |
| Pressure Cooker | 2 hours | pass |

The invention claimed is:

1. A polymeric resin obtained by curing at a temperature above 100° C. a compound of the formula

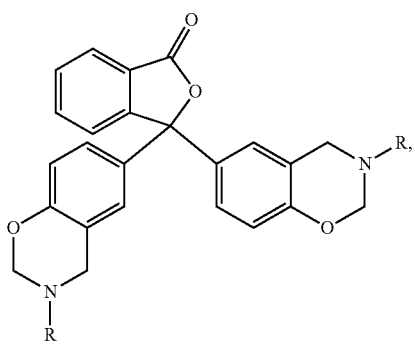

(I)

wherein R is, independently from one another, allyl, unsubstituted or substituted phenyl, unsubstituted or substituted $C_1$-$C_8$-alkyl or unsubstituted or substituted $C_3$-$C_8$-cycloalkyl.

2. The polymeric resin according to claim 1, wherein both substituents R are the same.

3. The polymeric resin according to claim 1, wherein R is phenyl.

4. The polymeric resin according to claim 1, wherein R is substituted by one to four substituents selected from the group consisting of amino, $C_1$-$C_4$-alkyl and allyl.

5. The polymeric resin according to claim 1, wherein the compound of formula (I) is obtained by: (i) reacting, under removal of water, and in the presence of a solvent and under pressure of up to about 100 psi, phenolphthalein with formaldehyde and a primary amine, whereby the molar ratio of phenolphthalein and formaldehyde is from 1:4.5 to 1:5 and the molar ratio of phenolphthalein and the primary amine groups is from 1:2.1 to 1:2.2.

6. The polymeric resin according to claim 5, whereby the primary amine is a compound of the formula $RNH_2$ (II), wherein R is allyl, unsubstituted or substituted phenyl, unsubstituted or substituted $C_1$-$C_8$-alkyl or unsubstituted or substituted $C_3$-$C_8$-cycloalkyl.

7. A process for preparing a flame retarded casting or laminate by thermally curing a compound of the formula

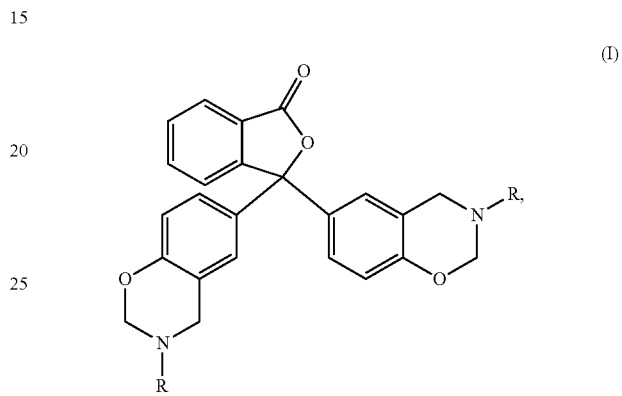

(I)

wherein R is, independently from one another, allyl, unsubstituted or substituted phenyl, unsubstituted or substituted $C_1$-$C_8$-alkyl or unsubstituted or substituted $C_3$-$C_8$-cycloalkyl and optionally an additive selected from reinforcement fibers, a plasticizer, carbon black, graphite, a filler, a dyestuff, micro hollow spheres, a metal powder and a mixture thereof.

8. A laminating composition consisting of 30 to 80% by weight of a compound of the formula

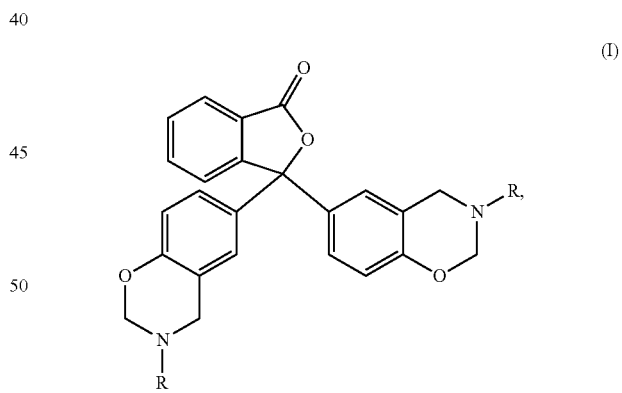

(I)

wherein R is, independently from one another, allyl, unsubstituted or substituted phenyl, unsubstituted or substituted $C_1$-$C_8$-alkyl or unsubstituted or substituted $C_3$-$C_8$-cycloalkyl and 0.1 to 50% by weight of ferrocene, and optionally a solvent or solvent mixture, a catalyst, a flame retardant, an epoxy resin, a filler or combinations thereof.

* * * * *